United States Patent
Simon

(10) Patent No.: US 9,629,581 B2
(45) Date of Patent: Apr. 25, 2017

(54) METHOD AND APPARATUS FOR BIOMETRIC MONITORING

(71) Applicant: Verizon Patent and Licensing Inc., Basking Ridge, NJ (US)

(72) Inventor: Adam J. Simon, Keller, TX (US)

(73) Assignee: VERIZON PATENT AND LICENSING INC., Basking Ridge, NJ (US)

( * ) Notice: Subject to any disclaimer, the term of this patent is extended or adjusted under 35 U.S.C. 154(b) by 667 days.

(21) Appl. No.: 14/140,000

(22) Filed: Dec. 24, 2013

(65) Prior Publication Data

US 2015/0173670 A1 Jun. 25, 2015

(51) Int. Cl.
| | |
|---|---|
| *G01C 9/00* | (2006.01) |
| *G01C 17/00* | (2006.01) |
| *G01C 7/00* | (2006.01) |
| *A61B 5/00* | (2006.01) |
| *A61B 5/11* | (2006.01) |
| *A61B 5/113* | (2006.01) |

(52) U.S. Cl.
CPC .......... *A61B 5/4806* (2013.01); *A61B 5/0022* (2013.01); *A61B 5/1116* (2013.01); *A61B 5/6801* (2013.01); *A61B 5/746* (2013.01); *A61B 5/113* (2013.01); *A61B 5/1112* (2013.01); *A61B 5/1121* (2013.01)

(58) Field of Classification Search
CPC ... A61B 5/4806; A61B 5/0022; A61B 5/1116; A61B 5/6801; A61B 5/746; A61B 5/1112; A61B 5/113; A61B 5/1121; G05D 1/0088; G05D 1/0094; G05D 1/0236; G05D 1/0238; G05D 1/0248; G05D 1/0272; G05D 1/0274; G05D 1/0276; G05D 1/042; G05D 1/0891; G05D 1/101; G05D 2201/0209; G05D 2201/0212; G05D 2201/0216

USPC ...................................... 702/150
See application file for complete search history.

(56) References Cited

U.S. PATENT DOCUMENTS

| | | | | |
|---|---|---|---|---|
| 2008/0208011 | A1* | 8/2008 | Shuler | A61B 5/0215 600/301 |
| 2009/0254003 | A1* | 10/2009 | Buckman | A61B 5/1117 600/595 |
| 2011/0178760 | A1* | 7/2011 | Schlumbohm | A61B 5/1117 702/141 |

* cited by examiner

*Primary Examiner* — Roy Y Yi

(57) ABSTRACT

An approach for monitoring a sleeping subject includes receiving an input for specifying an attachment position of a monitoring device attached to a subject, calibrating a resting positioning of the subject based on the attachment position, analyzing sensor information collected from the monitoring device to determine a movement of the subject into a potentially dangerous position with respect to the calibrated resting position, wherein the monitoring device includes an array of sensors including an accelerometer, one or more biometric sensors, or a combination thereof.

20 Claims, 14 Drawing Sheets

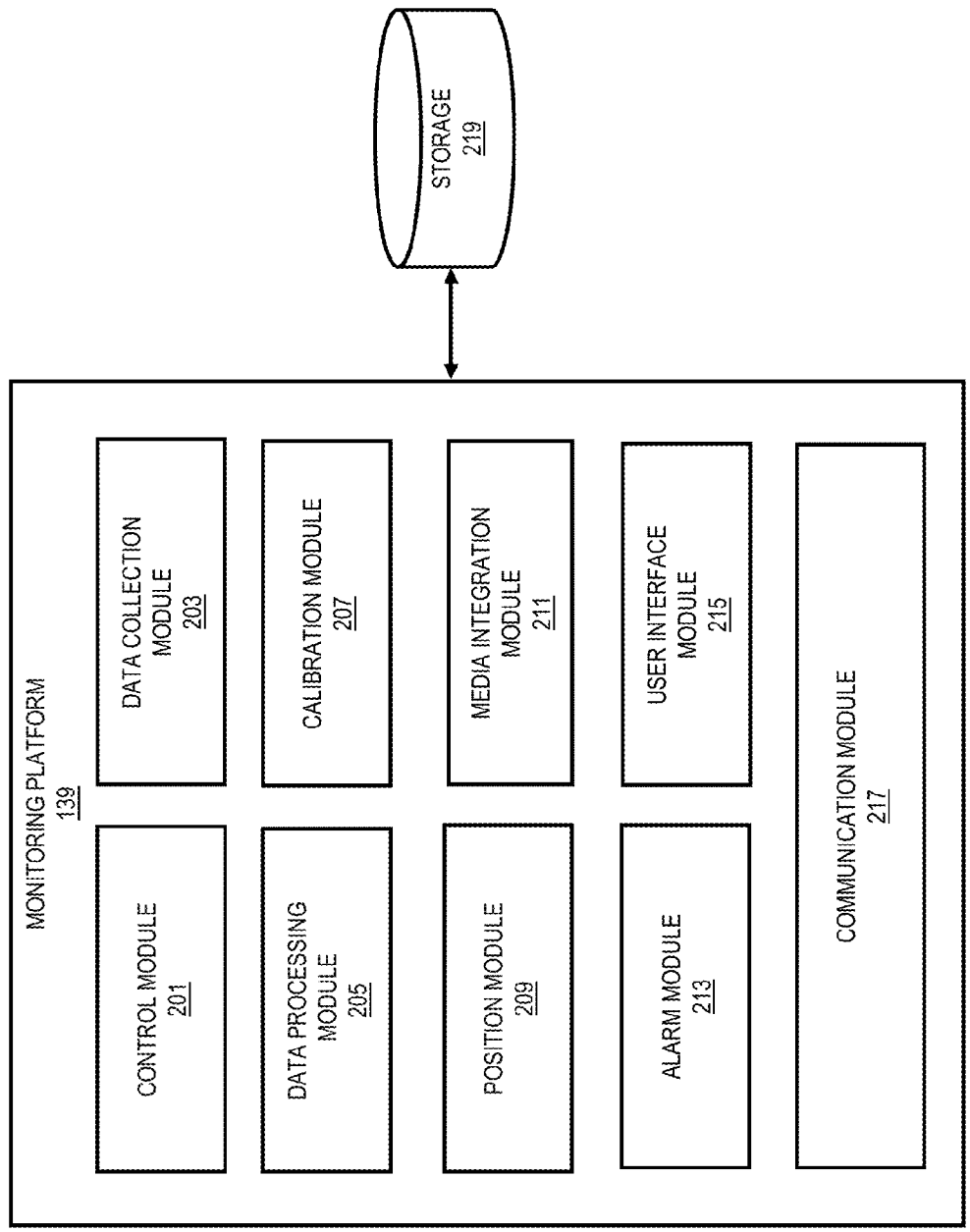

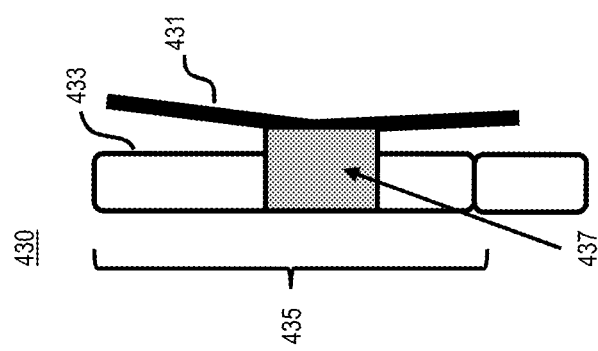
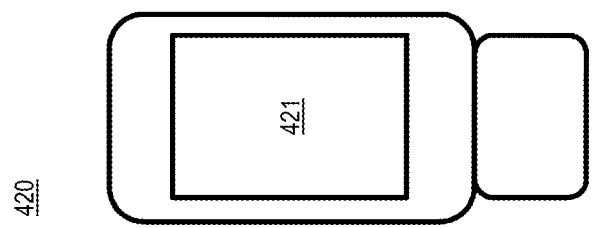
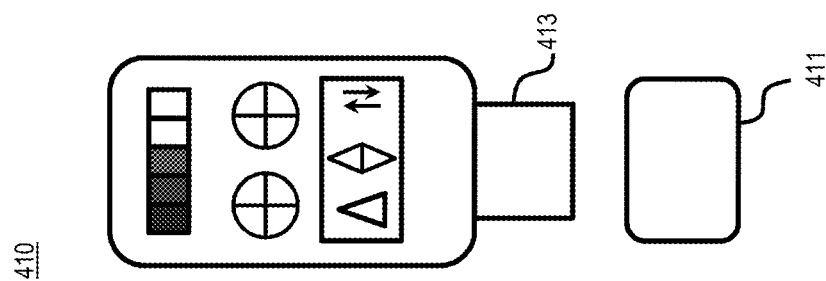
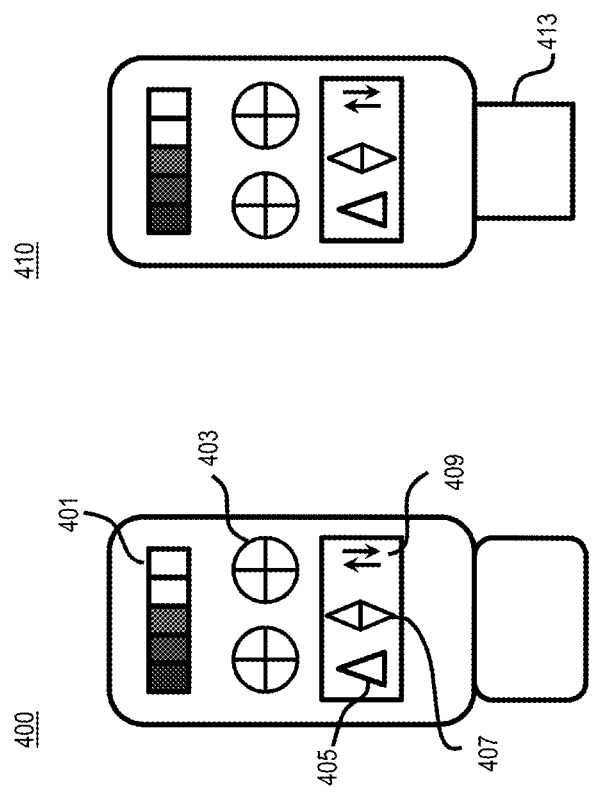

METHOD AND APPARATUS FOR BIOMETRIC MONITORING

BACKGROUND INFORMATION

Service providers are challenged to provide new services for a variety of personal uses. One such growing area is related to the collection and processing of biometric health and other sensory data. Growth in this area is being driven by the sales of biomedical devices and applications. A comprehensive understanding of certain sleep-related medical conditions is lacking. In particular, sudden infant death syndrome (SIDS) remains poorly understood and susceptible only to various suggested precautionary measures. For instance, parents are advised to place infants on their backs while they sleep. Therefore, parents and/or caregivers want to ensure that infants remain sleeping on their backs and do not change position. However, current sleep monitoring techniques for infants are costly and are not widely available.

Based on the foregoing, there is a need for a cost-effective and reliable monitoring service that provides early detection and alerting services for SIDS as well as other sleep-related disorders.

BRIEF DESCRIPTION OF THE DRAWINGS

Various exemplary embodiments are illustrated by way of example, and not by way of limitation, in the figures of the accompanying drawings in which like reference numerals refer to similar elements and in which:

FIG. 2 is a diagram of a platform capable of biometric monitoring, according to an exemplary embodiment;

FIGS. 4A through 4D illustrate a monitoring device, according to various exemplary embodiments;

DESCRIPTION OF THE PREFERRED EMBODIMENT

An apparatus, method, and software for integrated biometric monitoring, is described. In the following description, for the purposes of explanation, numerous specific details are set forth in order to provide a thorough understanding of the present invention. It is apparent, however, to one skilled in the art that the present invention may be practiced without these specific details or with an equivalent arrangement. In other instances, well-known structures and devices are shown in block diagram form in order to avoid unnecessarily obscuring the preferred embodiments of the invention.

Although the various exemplary embodiments are described with respect to processing biometric health data as collected by a service provider, it is contemplated that these embodiments have applicability to systems operated by different organizations and to other operations wherein biometric health data collection and processing is utilized. As used herein, the term "biometric data" or "biometric health data" may be used to refer to health-related data (e.g., heart rate, heart rhythm, temperature, oximeter, accelerometer, etc.) collected by a wearable, or otherwise attachable, device.

Figure 1A:
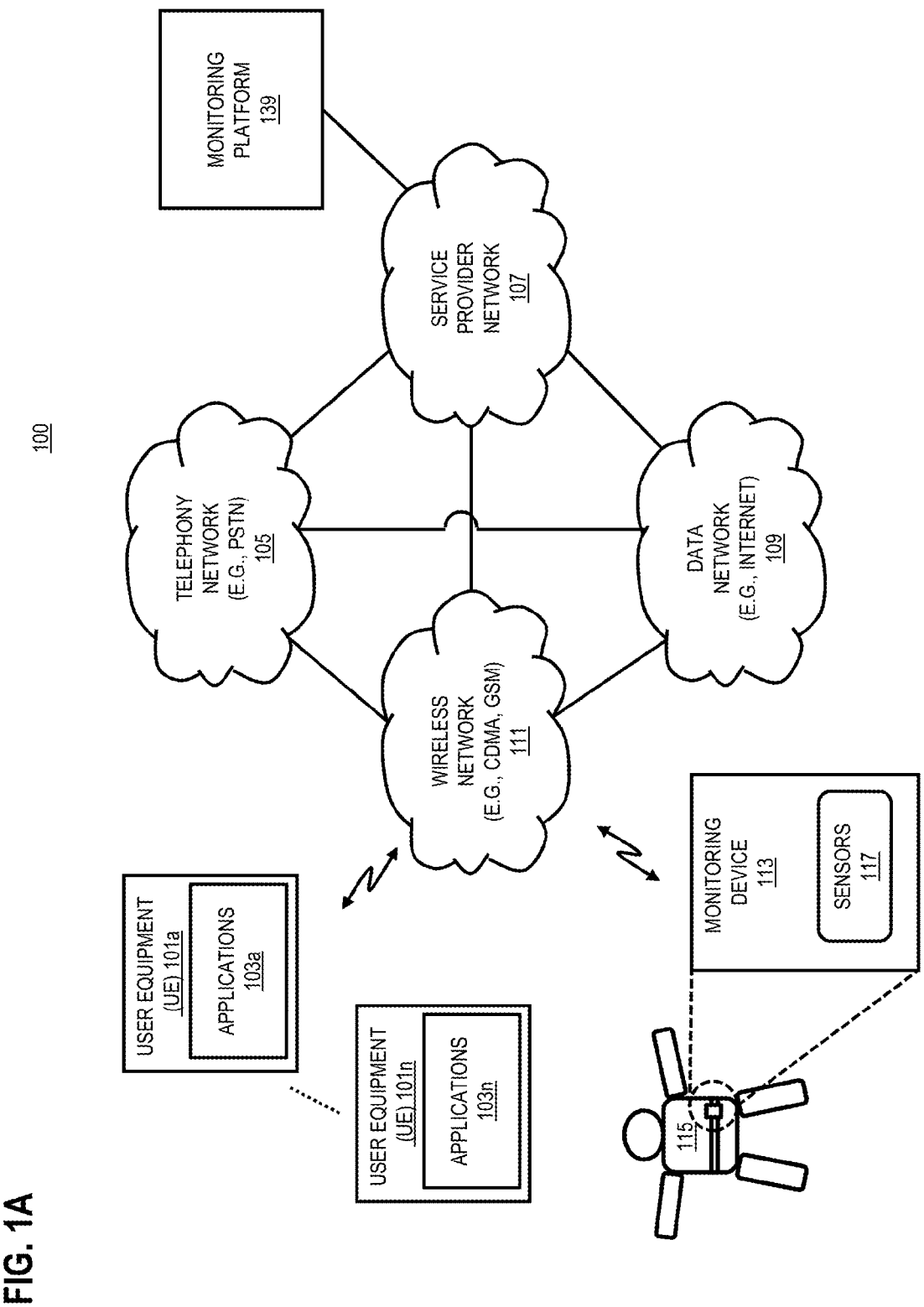
FIG. 1A is a diagram of a system capable of biometric monitoring, according to an exemplary embodiment.

FIG. 1A is a diagram of a system capable of biometric monitoring, according to an exemplary embodiment of the present disclosure. As shown, the system 100 comprises user equipment (UE) 101a-101n (collectively referred to as UE 101) that may include or be associated with applications 103a-103n (collectively referred to as applications 103). By way of example, the UE 101 is any type of mobile terminal, fixed terminal, or portable terminal including a mobile handset, station, unit, device, multimedia computer, multimedia tablet, Internet node, communicator, desktop computer, laptop computer, notebook computer, netbook computer, tablet computer, personal communication system (PCS) device, personal navigation device, personal digital assistants (PDAs), audio/video player, digital camera/camcorder, positioning device, television receiver, radio broadcast receiver, electronic book device, game device, or any combination thereof, including the accessories and peripherals of these devices, or any combination thereof. It is also contemplated that the UE 101 can support any type of interface to the user (such as "wearable" circuitry, etc.). In one embodiment, the applications 103 may be any type of application that is executable at the UE 101.

According to exemplary embodiments, end user devices may be utilized to communicate over system 100 and may include any customer premise equipment (CPE) capable of sending and/or receiving information over one or more of networks 105-111. For instance, a voice terminal may be any suitable plain old telephone service (POTS) device, facsimile machine, etc., whereas mobile device (or terminal) may be any cellular phone, radiophone, satellite phone, smart phone, wireless phone, or any other suitable mobile device, such as a PDA, pocket personal computer, tablet, customized hardware, etc. Further, computing device may be any suitable computing device, such as a VoIP phone, skinny client control protocol (SCCP) phone, session initiation protocol (SIP) phone, IP phone, personal computer, softphone, workstation, terminal, server, etc.

By way of example, the monitoring device 113 may be a device attached to a monitored subject (hereinafter referred to as "subject") 115 for the collection of biometric health data. In one embodiment, the monitoring device 113 includes one or more biometric health sensors (hereinafter also referred to as "biosensors") and has a wireless communication capability. For instance, the monitoring device 113 may include heart rate, body temperature, blood pressure, pulse rate, and oxygen sensors 117. By way of example, the sensors 117 may also include various global and local positioning sensors. In one embodiment, the sensors 117 include various positioning sensors that may be used to obtain the spatial position of the monitoring device 113 as determined by various positioning systems, including global positioning system (GPS), global navigation satellite system (GLONASS), among others. Thus, sensors 117 may include a GPS or GLONASS receiver to obtain positioning information from a global navigation satellite system (not shown for illustrative convenience). The monitoring device 113 may also include various local positioning or motion sensors. For instance, a gyrometer (not shown for illustrative convenience) may be used to determine the orientation (as measured by yaw, pitch, and roll angle measurements) of the monitoring device 113. In one embodiment, the local positioning or motion sensors may be utilized to infer or otherwise determine a sleeping or resting position (e.g., on back, stomach, side) of the subject 115.

Figure 1B:
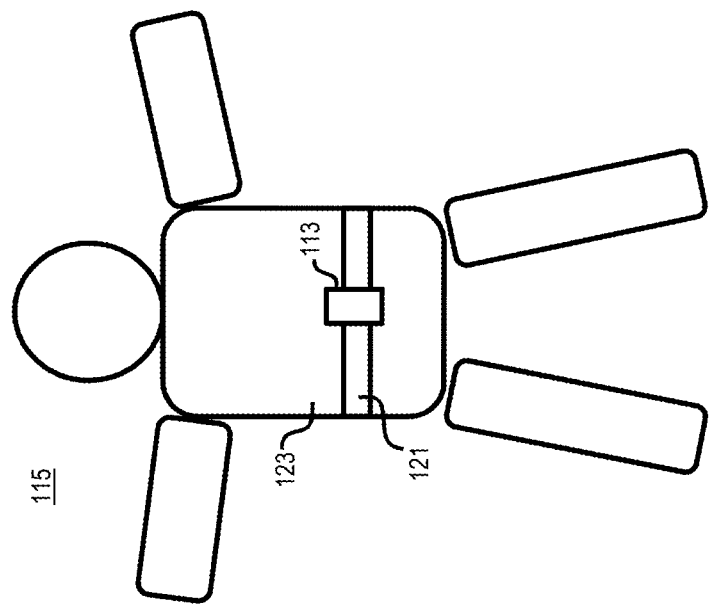
FIGS. 1B through 1D illustrate monitoring positions on a subject, according to exemplary embodiments.
Figure 1C:
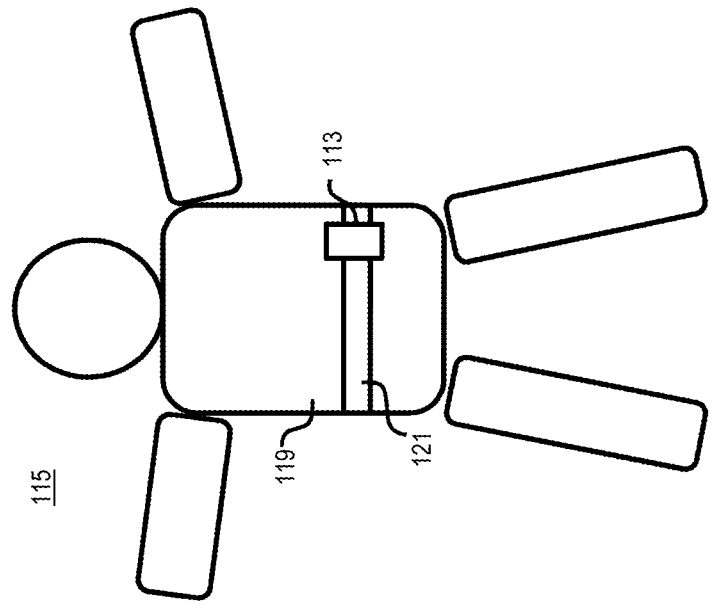

In certain instances, a particular sleeping position may be prescribed by healthcare providers as a precautionary measure against SIDS. For example, parents are strongly advised to place infants on their backs for at least the first few months after they are born. FIG. 1B illustrates the monitoring device 113 attached to the front 119 of the subject 115, according to an exemplary embodiment. The subject 115 may then be placed flat on his or her back with the monitoring device 113 located on the abdomen by means of an attachment article 121 (e.g., belt, strap). FIG. 1C illustrates the monitoring device 113 attached to a back 123 of the subject 115, according to an exemplary embodiment.

The specific position of the monitoring device 113 on the subject's body may impact the interpretation of biometric data. For instance, breathing dynamics may have a greater impact on accelerometer readings if the device is placed on the subject's abdomen versus its back. In addition, various biometric parameters such as body temperature may have to be adjusted or otherwise interpreted differently if the monitoring device is placed near the core of the body (e.g., abdomen, back, chest, etc.) versus an extremity (e.g., arm, leg).

By way of example, data from an accelerometer in the monitoring device 113 may be used to distinguish between general restlessness and a change of sleeping position of the subject 115. For example, accelerometer readings may be filtered to remove expected variations caused by movement of the diaphragm during breathing. On the other hand, a rapid or sudden change in the reading may indicate an unexpected or undesirable movement that results in a change of position. In one embodiment, the change of position may be confirmed based on accelerometer data in combination with orientation information reported by a gyrometer. For example, a jump in accelerometer readings may be observed to occur at approximately the same time as a change of an orientation. In another embodiment, additional confirmation may be received based on video monitoring of the subject 115. For example, the UE 101 may receive a video or image captured at the time of the detected activity such that a user may obtain visual confirmation that the subject has changed sleeping position.

In one embodiment, biometric, acceleration, and orientation data may be collected by sensors and communicated to the monitoring device 113 via a short-range communication link. FIG. 1D illustrates one or more sensors 125 arranged in an array, according to an exemplary embodiment. The subject 115 is, for instance, placed flat on his or her back and the sensors 125 are attached by means of an attachment article 127 (e.g., belt, strap, etc.) worn around the waist. In one embodiment, the sensors 125 collect data and communicate it to a separate monitoring device 129 via a short-range wireless or wire connection 131. As in the case of the monitoring device 113, the sensors 125 may also be worn on the back of the subject. It is contemplated that the sensors 125 may be placed on other, different, parts of the body and the data collected at each sensor may be separately processed and adjusted (if needed) based on the specific part of the body where it was collected.

Figure 1E:
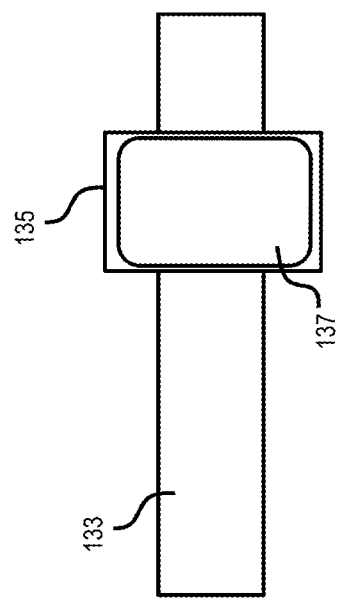
FIG. 1E is a diagram of an attachment article for wearing a monitoring device, according to an exemplary embodiment.
Figure 1D:
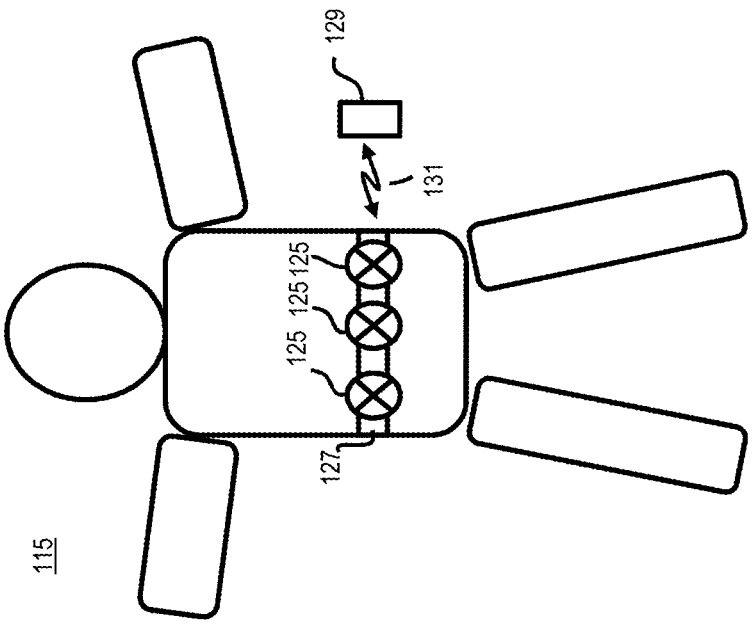

FIG. 1E illustrates an attachment article for wearing a monitoring device, according to an exemplary embodiment. In one embodiment, the attachment article includes a belt 133 with a holster 135 for carrying a monitoring device 137. The holster may allow direct contact of one or more biosensors located on the monitoring device 137 with the subject's skin by means of openings (not shown for illustrative convenience) in the holster 135. To ensure accurate data, a parent may ensure that one or more biosensors (not shown for illustrative convenience) of the monitoring device 113 are securely in contact with the subject. It is contemplated that various other attachment articles may be designed to accommodate monitoring device and/or biosensors of different sizes and attachment requirements.

In one embodiment, the monitoring device 113 and the UE 101 are capable of exchanging biometric and sensor data over the networks 105-111. For illustrative purposes, the networks 105-111 may be any suitable wireline and/or wireless network, and be managed by one or more service providers. For example, telephony network 105 may include a circuit-switched network, such as the public switched telephone network (PSTN), an integrated services digital network (ISDN), a private branch exchange (PBX), or other like network. Wireless network 111 may employ various technologies including, for example, code division multiple access (CDMA), enhanced data rates for global evolution (EDGE), general packet radio service (GPRS), mobile ad hoc network (MANET), global system for mobile communications (GSM), Internet protocol multimedia subsystem (IMS), universal mobile telecommunications system (UMTS), etc., as well as any other suitable wireless medium, e.g., microwave access (WiMAX), wireless fidelity (WiFi), satellite, and the like. Meanwhile, data network 109 may be any local area network (LAN), metropolitan area network (MAN), wide area network (WAN), the Internet, or any other suitable packet-switched network, such as a commercially owned, proprietary packet-switched network, such as a proprietary cable or fiber-optic network.

Although depicted as separate entities, networks 105-111 may be completely or partially contained within one another, or may embody one or more of the aforementioned infrastructures. For instance, the service provider network 107 may embody circuit-switched and/or packet-switched networks that include facilities to provide for transport of circuit-switched and/or packet-based communications. It is further contemplated that networks 105-111 may include components and facilities to provide for signaling and/or bearer communications between the various components or facilities of system 100. In this manner, networks 105-111 may embody or include portions of a signaling system 7 (SS7) network, or other suitable infrastructure to support control and signaling functions.

The approach of the system 100 stems, in part, from the recognition that biometric data may be utilized to detect and prevent certain syndromes that occur unexpectedly, particularly in the case of newborn infants. SIDS is one such example, but it is contemplated that other potentially life-threatening conditions may also be monitored using the techniques described herein. The approach of the system 100 further stem from the recognition that existing sleep monitoring techniques are costly and physically cumbersome, particular in relation to monitoring very young children.

An apparatus, method, and software for biometric monitoring are described. In the following description, for the purposes of explanation, numerous specific details are set forth in order to provide a thorough understanding of the present invention. It is apparent, however, to one skilled in the art that the present invention may be practiced without these specific details or with an equivalent arrangement. In other instances, well-known structures and devices are shown in block diagram form in order to avoid unnecessarily obscuring the present invention. As shown in FIG. 1A, the system 100 includes a monitoring platform 139 implemented as, for example, part of a service provider network 107. However, in alternative embodiments, the monitoring platform 139 could be implemented as any part of the system 100.

In one embodiment, the UE 101 has connectivity to monitoring platform 139 via networks 105-111. The monitoring platform 139 performs one or more functions associated with detecting trends in biometric data of a subject that is sleeping. For example, the monitoring platform 139 may be utilized to detect and report a potential onset of SIDS in a sleeping infant based on various physical or biometric indicators. The monitoring platform 139 may be used in other cases where early detection of biometric data may be utilized by a caregiver, guardian, parent, or health provider to avert a sleep-related injury or syndrome.

In one embodiment, the monitoring platform 139 receives an input for specifying an attachment position of the monitoring device 113 attached to the subject 115. The monitoring platform 139 calibrates a resting position of the subject based on the attachment position. For example, the monitoring platform 139 may use the attachment position to determine the average values for various biometric parameters, including heart rate, blood pressure, and body temperature. The monitoring platform 139 may then analyze sensor information collected from the monitoring device 113 to determine a movement of the subject 115 into a potentially dangerous position with respect to the calibrated resting position. As used herein, the term "potentially dangerous position" may be used to refer to sleeping positions that are associated with one or more sleep-related issues. The association may be based on medical studies or scientific evidence that suggests certain sleeping positions are more vulnerable to sleep-related disorders. In one embodiment, the monitoring device 113 includes the array of sensors 125, including an accelerometer, one or more biometric sensors, or a combination thereof. The sensor information may include accelerometer data, biometric data, or a combination thereof. In one embodiment, the monitoring platform 139 may determine the potentially dangerous position based on the accelerometer data and analyze the biometric data to confirm the potentially dangerous position. Alternatively, in another embodiment, the monitoring platform 139 may determine a downward trend of the biometric data extracted from the sensor information and confirm the potentially dangerous position based on the downward trend.

In one embodiment, the monitoring platform 139 may present a user interface providing a first representation of the subject 115, a second representation of the monitoring device 113, or a combination thereof, at the UE 101, wherein the input for specifying the attachment position is indicated via the user interface. The UE 101 may, for instance, present an interface whereby a user may specify the attachment position on the body of the subject 115. The UE 101 may also present image data of the subject 115. In one embodiment, the monitoring platform 139 may analyze image data of the subject 115 to confirm a potentially dangerous position, the sensor information, or a combination thereof. For instance, a user may use the image data of the subject to gauge whether the subject 115 has actually moved.

In one embodiment, the monitoring device 113 transmits the captured biometric date wirelessly via the networks 105-111 to the monitoring platform 139. Attachment to the subject 115 may be via an article of clothing, or directly to the skin surface. In one embodiment, the monitoring device 113 is a portable communication device (e.g., mobile phone, PDA, etc.) with integrated biometric health sensors. In another embodiment, the biometric data may be collected by one or more sensors and then communicated via a local wireless (e.g., Bluetooth™) or wire connection (e.g., universal serial bus (USB)) to a separate mobile device with connectivity to the monitoring platform 139.

FIG. 2 is a diagram depicting the components of a monitoring platform 139, according to one embodiment. The monitoring platform 139 includes various executable modules for performing one or more computing, data processing and network based instructions that in combination provide a means for biometric monitoring, as described in FIGS. 3A through 3E. Such modules can be implemented in hardware, firmware, software or a combination thereof. By way of example, the platform 139 may include a control module 201, a data collection module 203, a data processing module 205, a calibration module 207, a position module 209, a media integration module 211, an alarm module 213, a user interface module 215, and a communication module 217. These modules 201-217 can interact with storage 219 in support of their functions. According to some embodiments, the storage 219 is maintained and updated based on one or more transactions conducted with the UE 101 pertaining to various applications and functions of the monitoring device 113.

In one embodiment, the control module 201 controls the operations of the various other modules of the monitoring platform 139, including triggering execution of different modules accordingly. For example, the control module 201 directs the data processing module 205 to process received biometric health data and cause the user interface module 215 to present the data at a user interface at the UE 101.

In one embodiment, the data collection module 203 may be used to interact with various biometric sensors to collect biometric data. For example, the data collection module 203 may interact with a mobile application installed at the monitoring device 113. The mobile application may sample biometric data at one or more biosensors at regular intervals (e.g., 5-10 seconds). The sampled data may then be forwarded to the data collection module 203 via the networks 105-111. In one embodiment, the data collection module 203 is a server-side application and is separate from a client-side application installed at the monitoring device 113. The selection of sampling interval may be based on a desired level of accuracy and responsiveness. If the sleeping position and the biometric data must be closely monitored, the sampling interval can be reduced to more closely track fluctuations. On the other hand, a less data-intensive monitoring can be performed by increasing the sampling interval.

In one embodiment, the data processing module 203 is utilized to process and analyze biometric health data from the monitoring device 113. For instance, the data processing module 205 may interact with the data collection module 203 to process heart rate, pulse, temperature, accelerometer, and gyrometer data collected at the monitoring device 113 and received at the monitoring platform 139 via networks 105-111. In one embodiment, the data is smoothed via a filtering process to remove transient and minor variations. The smoothed data may then be analyzed to obtain resting state body temperature, heart rate, and other variables. In one embodiment, the data processing module 205 interacts with the user interface module 215 to cause the data to be presented at a UE 101. For instance, the data may be displayed according to various user interface templates. The data processing module 205 may also be used to detect a change in sleeping position. For example, the biometric health data received from the monitoring device 113 may indicate a sharp or sudden downward trend with respect to one or more indicators (e.g., heart rate) if the subject has moved into a potentially dangerous position. In one embodiment, the data processing module 205 continually measures (e.g., moving average) and detects trends in the data. The data processing module 205 may indicate the trend to the control module 201 and/or interact with one or more other modules (e.g., alarm module 213) to generate an alert.

In one embodiment, the calibration module 207 may be used to calibrate the monitoring device 113. For instance, the calibration module 207 may calibrate each collected biometric health data parameter as well as any position or orientation sensors of the monitoring device 113. Data for each parameter may be received separately or as a single data stream from the monitoring device 113. Then, the calibration module 207 may interact with the data processing module 205 to sample and filter the data for one or more time intervals. Data collected during these intervals may be smoothed by application of digital filtering and then statistically analyzed to determine average and standard deviation values. Using these values, the calibration module 207 may interact with the alarm module 213 to set threshold values for data trends indicative of a potentially dangerous sleeping position. For example, the threshold value for an oxygen level may be set such that a sharp downward trend is quickly recognized. Other threshold values may be set to indicate changes in the health of the subject.

The position module 209 may be used to determine a sleeping position of a subject. In one embodiment, the position module 209 interacts with the data processing module 205 to determine whether biometric data indicates any change in sleeping position. For example, accelerometer data may indicate that the subject has moved or is attempting to move. In addition, gyrometer data may indicate a change of orientation that can be correlated with the accelerometer data. The correlated data may indicate that there has not been any significant change in sleeping position. In one embodiment, based on the determination, the position module 209 may interact with the user interface module 215 to present the sleeping position at a UE. For instance, the UE may be caused to display a message "Kailee is sleeping on her back." The UE may also be caused to display one or more status messages, including color-coded safety indicators. For example, a low-risk sleeping position may be indicated by a green background for the display.

In one embodiment, the position module 209 may determine an initial sleeping position based on input from a user. For instance, a user may provide input that indicates an attachment position of the monitoring device 113 on the subject 115. The input may be provided at a UE. For instance, a user may indicate an attachment position on a representation of the subject via a touch-sensitive display. Alternatively, the attachment position may be selected from a list of entries (e.g., stomach, leg, ankle, arm, etc.) displayed at the UE. The input may be provided, for example, by a parent user as an infant subject is being prepared for sleep at night. Upon receiving the indicated position, the position module 209 may record the information in the storage 219 and associate it with a particular user session. In one embodiment, other modules may utilize the attachment position to calibrate the monitoring device 113. For instance, the attachment position may be communicated to the calibration module 207 and the data processing module 205 to initialize an initial sleeping position and to determine baseline biometric values.

In one embodiment, the subject's biometric data may be tagged based on the attachment position of the monitoring device 113. Thus tagged, the biometric data may be used to calibrate the monitoring device 113 based on the attachment position. A baseline or average value for each data parameter can be established for a particular attachment position. For example, if the monitoring device 113 is attached on the side (e.g., hip) of an infant, the data processing module 205 may set device orientation information to the baseline resting position. Similarly, other biometric health variables such as skin temperature may be calibrated for the monitoring device 113. In one embodiment, the position module 209 may communicate the attachment position to the alarm module 213 to set one or more alarm threshold values. For example, an alarm threshold for orientation data may be set according to the expected range of orientations for an attachment position on a core portion (e.g., abdomen, hip, etc.) versus on an extremity (e.g., arm, ankle, etc.).

In one embodiment, the media integration module 211 may be used to integrate a video or image stream with biometric data. For example, the video or image stream may be obtained of the subject via a real-time image acquisition unit (e.g., webcam, camera, etc.) and communicated to the monitoring platform 139. The captured images may then be synchronized with the biometric data also being received from the subject. After integration, the combined data and video/image data may be communicated to a UE for display. In one embodiment, a user may utilize the video/image data to confirm the reported sleeping position of the subject. For example, the video/image data may only be displayed at the UE upon request if biometric data indicates that the infant is attempting to turnover or has turned over to sleep on a different body surface. Alternatively, the biometric data may be utilized to confirm a dangerous sleeping position upon request. For example, a user may continuously receive a video stream of the subject, but only receives the biometric data upon request.

In one embodiment, the alarm module 213 may be used to generate an alarm or warning message that the subject is not sleeping in a safe position or that the biometric data is showing a sharp downward trend. For instance, an email or an SMS text message may be generated and sent to the user at a registered email account or phone number. The message may indicate the change in position to the user such that the user can take appropriate steps. In one embodiment, the alarm module 213 receives an indication from the data processing module 205 that a change in biometric health data is being observed. The alarm module 213 may respond to this indication by testing the data against various threshold values. If one or more thresholds are satisfied, the alarm module 213 may then cause the warning message to be generated. In one embodiment, the alarm module 213 interacts with the calibration module 207 to set the threshold values. For instance, the calibration module 207 may determine average data values for one or more critical biometric data variables (e.g., heart rate, temperature). The alarm module 213 may access the averaged values and determine appropriate thresholds.

In one embodiment, the user interface module 215 facilitates generation of various interfaces for enabling users to interact with the monitoring platform 139. This includes, for example, generation of a login interface for enabling user registration and/or access to one or more services associated with the monitoring platform 139. By way of example, the user interface module 215 may generate different user interface elements for selection by registered users. It is noted that the user interface module 215 may be activated by way of various APIs or other function calls at a computing device of the third party content provider.

In one embodiment, the user interface module 215 facilitates generation of an interface to present biometric health data regarding a monitored subject. For instance, the interface may include heart rate, temperature, sleeping status (e.g., sleeping, restless, aware, etc.). The interface may also include a status message (e.g., "Kailee is sleeping on her back"). Other information may include a battery status for the monitoring device 113. The interface may be color coded to highlight normal or abnormal readings taken at the subject. For example, a green light may be used to highlight normal biometric data and a red or amber for abnormal variation in the received data. In one embodiment, the user interface module 215 also causes the interface of the UE to present an integrated video/image stream of the subject. The video stream may provide an extra layer of security and comfort to the user that the subject is sleeping well. Alternatively, the video stream may alert the user quickly to any serious situations.

In one embodiment, the communication module 217 executes various protocols and data sharing techniques for enabling collaborative execution between the monitoring platform 139, the UE 101 and the monitoring device 113. In addition, the communication module 217 enables generation of signals for communicating with various elements of the service provider network, including various gateways, policy configuration functions and the like. In one embodiment, the communication module 217 allows the monitoring platform 139 to communicate with the UE 101 and the monitoring device 113 based on requests from a user. Alternatively, the communication module 217 may provide regular updates of status and data to the UE 101.

Although reference is made to a single subject, it is contemplated that the various modules of the monitoring platform 139 may be capable of simultaneously monitoring multiple devices or subjects. For instance, the monitoring platform 139 may be capable of receiving and processing data feeds from multiple monitoring devices attached to different subjects. The monitoring platform 139 may present the biometric data and status messages of each subject at one or more UE registered for that subject. It is further contemplated that the monitoring platform 139 may ensure privacy and confidentiality of the biometric data with various authentication and encryption techniques.

Figure 9:
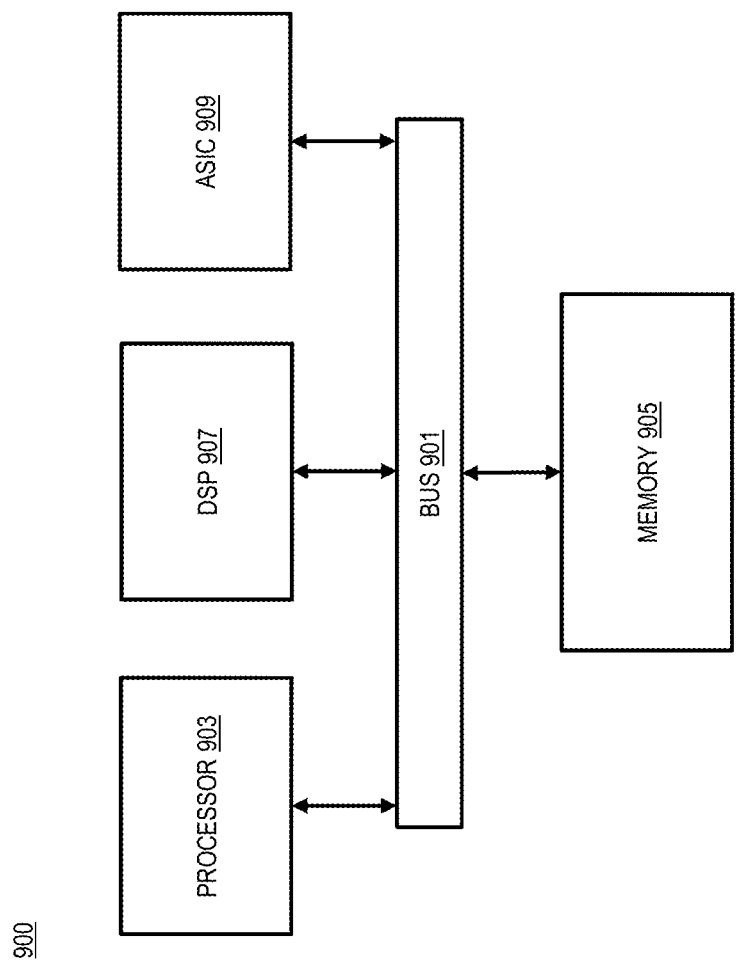
FIG. 9 is a diagram of a chip set that can be used to implement various exemplary embodiments.

FIGS. 3A through 3E illustrate flowcharts for biometric monitoring, according to an exemplary embodiment. In one embodiment, monitoring platform 139 performs the processes illustrated in FIGS. 3A through 3E and are implemented in, for instance, a chip set including a processor and a memory as shown in FIG. 9.

Figure 3A:
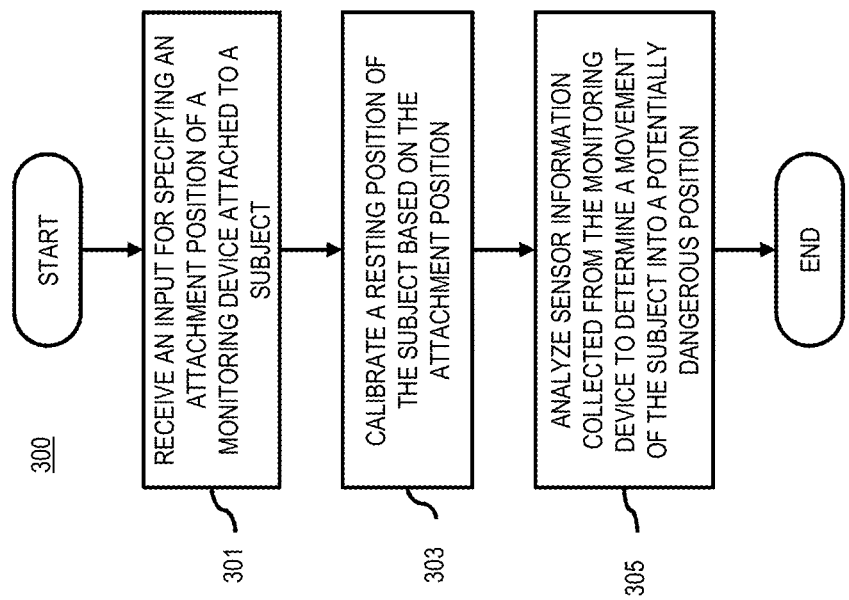
FIGS. 3A through 3E are flowcharts of processes for biometric monitoring, according to an exemplary embodiment.

FIG. 3A illustrates a process 300 for biometric monitoring, according to an exemplary embodiment. In step 301, the position module 209 of the monitoring platform 139 receives an input for specifying an attachment position of a monitoring device attached to a subject. In one embodiment, the input is provided at the UE 101 by a user (e.g., a parent) that wants to monitor the sleep of a subject (e.g., infant). The input may be indicated via a touch-screen display and may indicate specific parts of the body (e.g., wrist, arm, ankle, chest, abdomen, etc.) that the monitoring device 113 has been attached to. In step 303, the calibration module 207 of the monitoring platform 139 calibrates a resting position of the subject based on the attachment position. For example, the calibration module 207 may calibrate the monitoring device 113 based on biometric health data and/or other sensor information during an initial phase. The resting position may correspond to a proper and safe sleeping position of the subject (e.g., an infant placed on its back). In step 305, the data processing module 205 and the position module 209 of the monitoring platform 139 may analyze sensor information collected from the monitoring device to determine a movement of the subject into a potentially dangerous position. In one embodiment, the data processing module 205 tests biometric health data and accelerometer information to determine if the subject is moving into a different position. In one embodiment, the movement of the subject may be determined as a potentially dangerous position if the biometric health data indicates a sharp downward trend in one or more vital health indicators (e.g., heart rate). In another embodiment, the movement itself may be determined to be dangerous because the new position is associated with potentially dangerous health conditions such as SIDS.

Figure 3C:
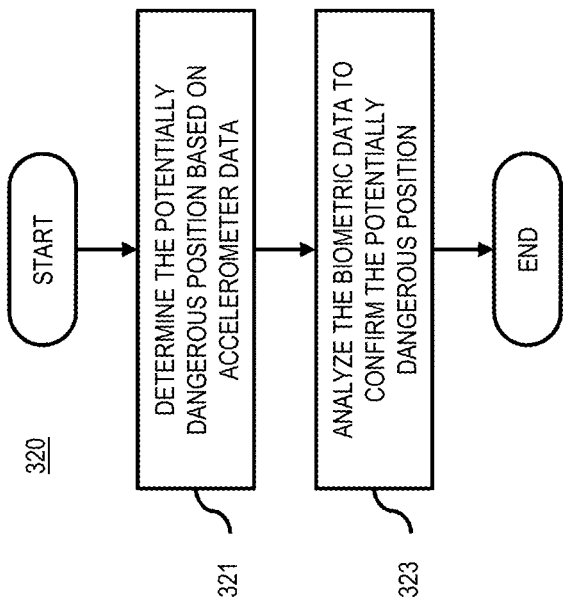
Figure 3B:
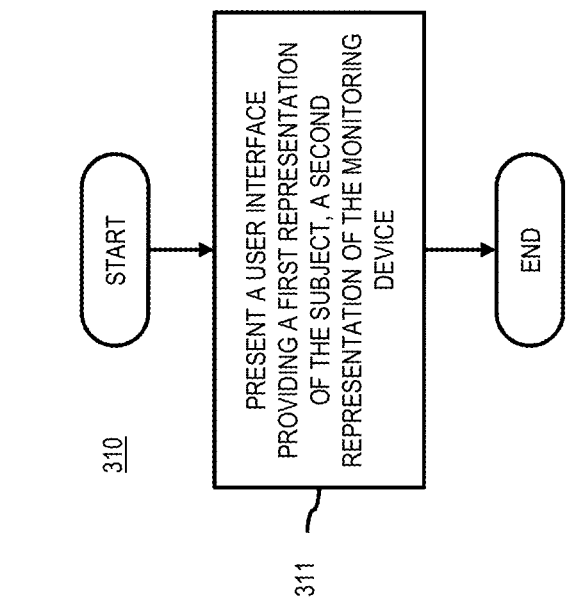

FIG. 3B illustrates a process 310 for biometric monitoring, according to an exemplary embodiment. In step 311, the user interface module 215 of the monitoring platform 139 presents a user interface providing a first representation of the subject, a second representation of the monitoring device, or a combination thereof. In one embodiment, a first representation may include a video or image of the subject. For instance, the media integration module 211 of the monitoring platform 139 may present real-time or captured image/video of the subject at the UE 101. In one embodiment, a second representation of the monitoring device 113 may also be presented at the UE. The second representation may include various status indicators related to the subject. For instance, a status message of the subject (e.g., "Kailee is sleeping restlessly") may be displayed along with various biometric indicators. A user may utilize the first and second representations to quickly assess the condition of the subject.

FIG. 3C illustrates a process 320 for biometric monitoring, according to an exemplary embodiment. In step 321, the position module 209 of the monitoring platform 139 determines a potentially dangerous position based on accelerometer data. The position module 209 may determine that the subject has moved into a dangerous position based on accelerometer and gyrometer data. For instance, the accelerometer may indicate that the subject has moved and the gyrometer may indicate a change of orientation. Based on this information, the position module 209 may determine that a change in sleeping position has occurred. In step 323, the data processing module 205 analyzes the biometric data to confirm the potentially dangerous position. To confirm the potentially dangerous position, the data processing module 205 may analyze the biometric health data of the subject. For instance, the monitoring device 113 may communicate a sharp downward trend in the oximeter and heart rate readings to the monitoring platform 139. In one embodiment, the data processing module 205 may interact with the position module 209 to determine that the sleeping position is a potentially dangerous position. In one embodiment, the data processing module 205 may interact with the alarm module 213 to generate a warning message to the user.

Figure 3E:
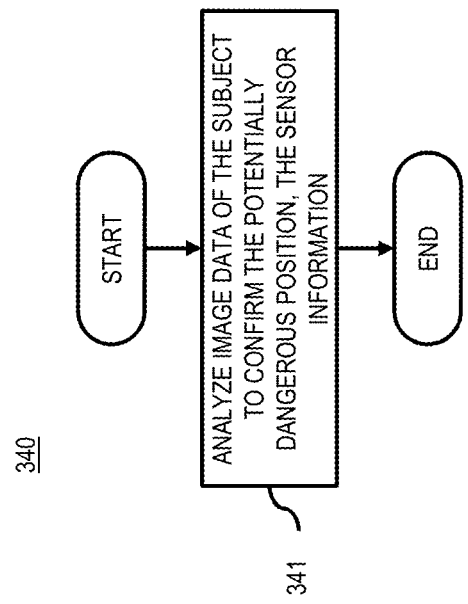
Figure 3D:
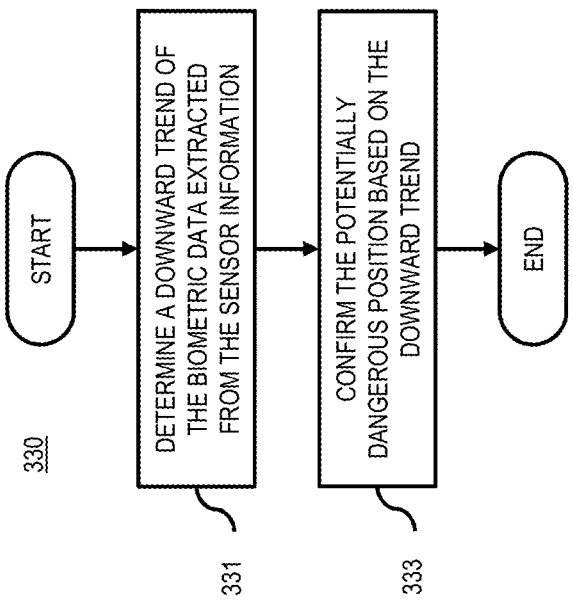

FIG. 3D illustrates a process 330 for biometric monitoring, according to an exemplary embodiment. In step 331, the data processing module 205 of the monitoring platform 139 may determine a downward trend of the biometric data extracted from the sensor information. A downward trend may be measured based on a moving average or other statistical indicator. For example, the data processing module 205 may access the resting state average values for one or more biometric parameters and compare it to the data being collected. In step 333, the position module 209 may interact with the data processing module 205 to confirm the potentially dangerous position based on the downward trend. For example, the position module 209 may examine position data collected at the subject by an accelerometer sensor and determine that the subject has moved into a potentially dangerous position. In one embodiment, the data processing module 205 may interact with the alarm module 213 to send an alarm message to the user.

FIG. 3E illustrates a process 340 for biometric monitoring, according to an exemplary embodiment. In step 341, the position module 209 may interact with the media integration module 211 of the monitoring platform 139 to analyze image data of the subject to confirm the potentially dangerous position, the sensor information, or a combination thereof. In one embodiment, the data processing module 205 receives video or other visual information of the subject and analyzes it. For example, the media data may be compared to an initial image captured when the monitoring device 113 was being calibrated. In one embodiment, the data processing module 205 may interact with the alarm module 213 to send an alarm message to the user. Alternatively, the media integration module 211 may receive the video information and interact with the user interface module 215 to present it at the UE. A user observing the image data may confirm the potentially dangerous position by also looking at biometric health data.

FIGS. 4A through 4D illustrate a monitoring device, according to an exemplary embodiment. FIG. 4A illustrates a front-view 400 of a monitoring device. At the top of the device is a battery life indicator 401 to indicate the amount of reserves remaining in the battery. In one embodiment, the battery life indicator 401 is an LED or LCD scale display with colors ranging from red (low reserves) to green (fully charged). The device may also include one or more toggles to control the monitoring device. In one embodiment, a power toggle 403 turns the device on and off. The monitoring device may also include one or more LED indicators. For example, the warning icon 405 may indicate if the device is affected by a technical failure (e.g., loss of biometric signal, failure of biosensor). In one embodiment, a connected icon 407 may indicate whether the monitoring device has established a local short-range connection to local device (e.g., computer, phone, etc.). For example, the monitoring device may communicate with the monitoring platform 139 via a local communication device (not shown for illustrative convenience) capable of connecting to a private 4G LTE network. In one embodiment, the local connection is a Bluetooth™ or infrared (e.g., IrDA) connection.

In one embodiment, the monitoring device is equipped with a USB port. FIG. 4B illustrates a front-view 410 of the monitoring device in FIG. 4A with a USB cap 411 removed, according to an exemplary embodiment. The USB connector 413 may be utilized to directly connect to another device. In one embodiment, a USB interface allows the monitoring device to be reconfigured by, for instance, software upgrades and data transfers. FIG. 4C illustrates a back-view 420 of a monitoring device, according to an exemplary embodiment. A biosensor 421 may be used to pick up electrical, temperature, or other data from a subject. In one embodiment, the biosensor 421 is placed in direct contact with the skin of the subject on any part of the body. For instance, the monitoring device may be placed on the chest of an infant. The data captured by the biosensor 421 may be transferred to the monitoring platform 139 via the networks 105-111.

FIG. 4D illustrates a side-view 430 of a monitoring device, according to an exemplary embodiment. In one embodiment, an attachment clip (or buckle) 431 allows the monitoring device to be clipped to an article of clothing of the subject. Alternatively, the attachment clip 431 may allow the device to be attached via a device holder strapped to the subject with a belt or other fastening system. In one embodiment, the attachment clip 431 is on the front-side 433 of the monitoring device such as to not interfere with a biosensor on the back-side 435. The attachment clip 431 may be designed to hold the monitoring device by means of holders 437 on the sides of the monitoring device.

Figure 5B:
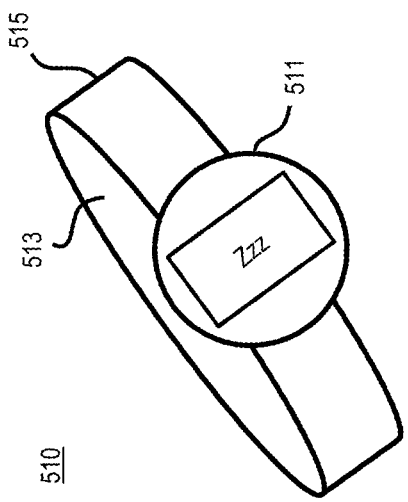
FIGS. 5A and 5B illustrate a strap monitoring device, according to various exemplary embodiments.
Figure 5A:
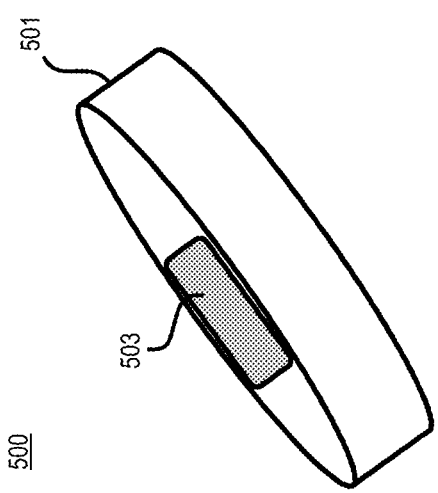

FIGS. 5A and 5B illustrate a strap monitoring device, according to an exemplary embodiment. FIG. 5A illustrates a strap monitoring device 500 with an elastic band 501 that can be worn on a wrist, upper or lower arm or leg. The elastic band 501 includes an integrated monitoring device 503 on the inside and can be made in a variety of sizes for subjects of different ages. FIG. 5B illustrates another strap monitoring device 510, according to an exemplary embodiment. In one embodiment, the device 510 may be worn as a wrist band with a display interface 511. For example, the display interface 511 may present a status (e.g., sleeping, awake, aware, etc.) based on one or more sensors (not shown for illustrative convenience) on an inner surface 513 of the strap 515. In one embodiment, the monitoring device 510 synchronizes and communicates with a cloud-based biometric monitoring application.

Figure 6A:
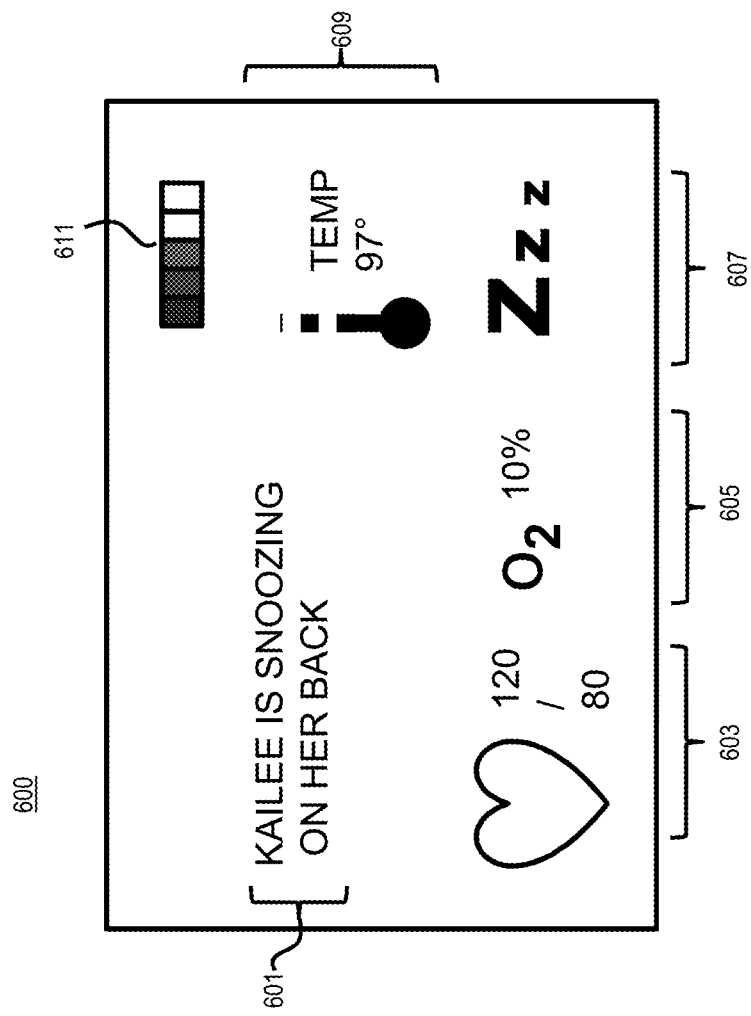
FIGS. 6A and 6B illustrate a user interface of a monitoring application, according to various exemplary embodiments.

FIG. 6A illustrates a user interface 600 presented at a display of a monitoring application, according to an exemplary embodiment. In one embodiment, a status message 601 presents the sleeping position of the subject being monitored. In addition, various biometric health parameters are displayed, including heart rate 603, oxygen level 605, sleep status 607, and body temperature 609. The sleep status 607 may include different levels of restfulness (e.g., sleeping, restless, aware). In one embodiment, the sleep status 607 is based on biometric or accelerometer data. A battery status 611 may also be displayed. In one embodiment, the user interface 600 may change the background color of the display based on the sleep status 607. For instance, the background may be given a green color to indicate that the subject is sleeping peacefully. On the other, amber or red colors may be used to indicate restless behavior or sustained agitation.

Figure 6B:
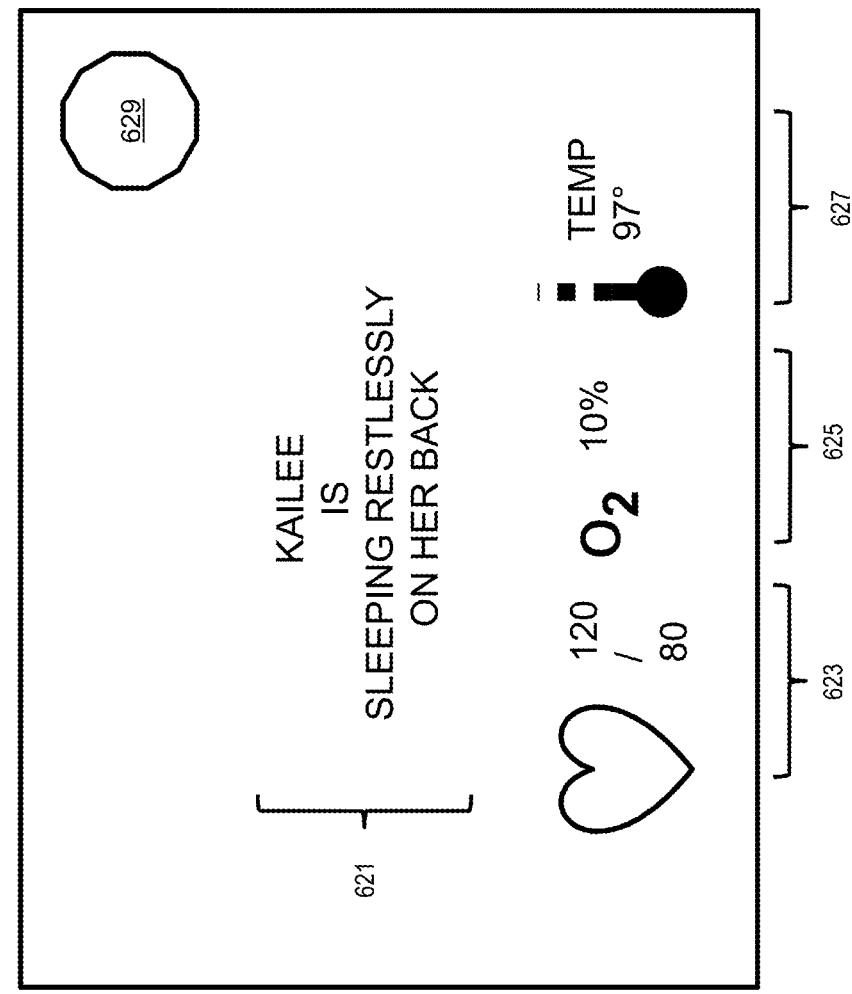

FIG. 6B illustrates a user interface 620 presented at a display of a monitoring application, according to another exemplary embodiment. A status message 621 that includes a sleeping position is displayed. In one embodiment, additional biometric parameters are displayed, including heart rate 623, oxygen level 625, and body temperature 627. The biometric monitoring system may be configured by selecting the settings control 629. For example, the user may select the type of alert (e.g., email, text message), display settings, biometric sampling interval, and the specific biometric parameters to monitor. In one embodiment, the background of the user interface 620 may be utilized to present image data of the subject. Alternatively, the image data may be presented in a small section of the display or minimized based on user preferences.

Figure 7:
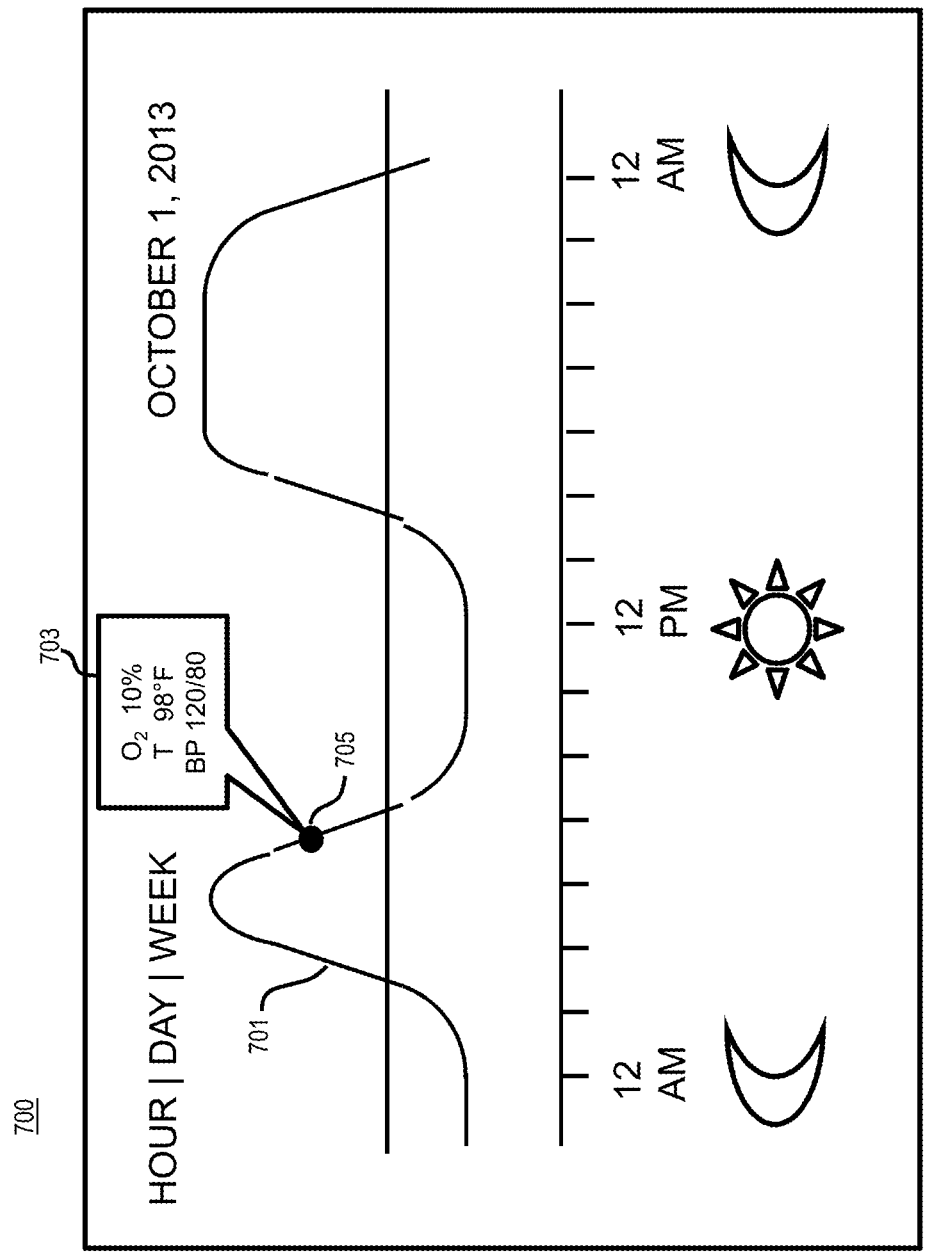
FIG. 7 illustrates a user interface for presentation of historical biometric data, according to exemplary embodiment.

FIG. 7 illustrates a user interface 700 for presentation of historical biometric data, according to an exemplary embodiment. Historical biometric and sleep pattern data may be presented in graph or numerical form and may be accessed by means of a menu item (or other selection control) at a user interface of the monitoring application. In one embodiment, the graph 701 is utilized to track sleep patterns over a twenty-four hour period. For instance, a sleep status (e.g., resting, aware, awake, etc.) may be indicated by levels of biometric activity. In one embodiment, the user may obtain more detailed breakdown 703 of the biometric parameters for a specific time by sliding and clicking a displayed marker 705 along the graph 701.

The computer system 800 may be coupled via the bus 801 to a display 811, such as a cathode ray tube (CRT), liquid crystal display, active matrix display, or plasma display, for displaying information to a computer user. An input device 813, such as a keyboard including alphanumeric and other keys, is coupled to the bus 801 for communicating information and command selections to the processor 803. Another type of user input device is a cursor control 815, such as a mouse, a trackball, or cursor direction keys, for communicating direction information and command selections to the processor 803 and for controlling cursor movement on the display 811.

According to an embodiment of the invention, the processes described herein are performed by the computer system 800, in response to the processor 803 executing an arrangement of instructions contained in main memory 805. Such instructions can be read into main memory 805 from another computer-readable medium, such as the storage device 809. Execution of the arrangement of instructions contained in main memory 805 causes the processor 803 to perform the process steps described herein. One or more processors in a multiprocessing arrangement may also be employed to execute the instructions contained in main memory 805. In alternative embodiments, hard-wired circuitry may be used in place of or in combination with software instructions to implement the embodiment of the invention. Thus, embodiments of the invention are not limited to any specific combination of hardware circuitry and software.

Figure 8:
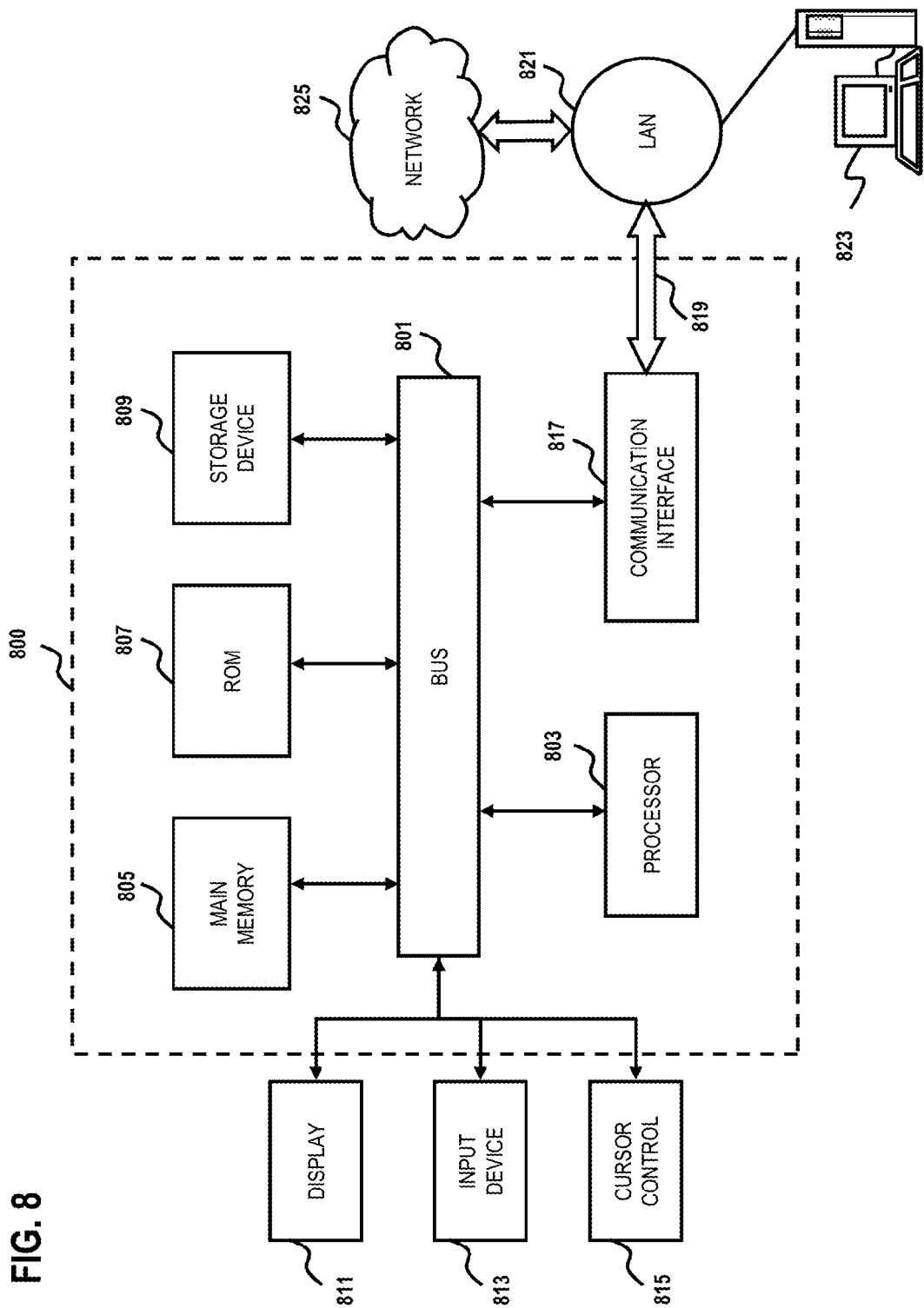
FIG. 8 is a diagram of a computer system that can be used to implement various exemplary embodiments.

The computer system 800 also includes a communication interface 817 coupled to bus 801. The communication interface 817 provides a two-way data communication coupling to a network link 819 connected to a local network 821. For example, the communication interface 817 may be a digital subscriber line (DSL) card or modem, an ISDN card, a cable modem, a telephone modem, or any other communication interface to provide a data communication connection to a corresponding type of communication line. As another example, communication interface 817 may be a LAN card (e.g. for Ethernet™ or an Asynchronous Transfer Model (ATM) network) to provide a data communication connection to a compatible LAN. Wireless links can also be implemented. In any such implementation, communication interface 817 sends and receives electrical, electromagnetic, or optical signals that carry digital data streams representing various types of information. Further, the communication interface 817 can include peripheral interface devices, such as a USB interface, a PCMCIA (Personal Computer Memory Card International Association) interface, etc. Although a single communication interface 817 is depicted in FIG. 8, multiple communication interfaces can also be employed.

The network link 819 typically provides data communication through one or more networks to other data devices. For example, the network link 819 may provide a connection through local network 821 to a host computer 823, which has connectivity to a network 825 (e.g. a WAN or the global packet data communication network now commonly referred to as the "Internet") or to data equipment operated by a service provider. The local network 821 and the network 825 both use electrical, electromagnetic, or optical signals to convey information and instructions. The signals through the various networks and the signals on the network link 819 and through the communication interface 817, which communicate digital data with the computer system 800, are exemplary forms of carrier waves bearing the information and instructions.

The computer system 800 can send messages and receive data, including program code, through the network(s), the network link 819, and the communication interface 817. In the Internet example, a server (not shown) might transmit requested code belonging to an application program for implementing an embodiment of the invention through the network 825, the local network 821 and the communication interface 817. The processor 803 may execute the transmitted code while being received and/or store the code in the storage device 809, or other non-volatile storage for later execution. In this manner, the computer system 800 may obtain application code in the form of a carrier wave.

The term "computer-readable medium" as used herein refers to any medium that participates in providing instructions to the processor 803 for execution. Such a medium may take many forms, including but not limited to non-volatile media, volatile media, and transmission media. Non-volatile media include, for example, optical or magnetic disks, such as the storage device 809. Volatile media include dynamic memory, such as main memory 805. Transmission media include coaxial cables, copper wire and fiber optics, including the wires that comprise the bus 801. Transmission media can also take the form of acoustic, optical, or electromagnetic waves, such as those generated during radio frequency (RF) and infrared (IR) data communications. Common forms of computer-readable media include, for example, a floppy disk, a flexible disk, hard disk, magnetic tape, any other magnetic medium, a CD-ROM, CDRW, DVD, any other optical medium, punch cards, paper tape, optical mark sheets, any other physical medium with patterns of holes or other optically recognizable indicia, a RAM, a PROM, and EPROM, a FLASH-EPROM, any other memory chip or cartridge, a carrier wave, or any other medium from which a computer can read.

Various forms of computer-readable media may be involved in providing instructions to a processor for execution. For example, the instructions for carrying out at least part of the embodiments of the invention may initially be borne on a magnetic disk of a remote computer. In such a scenario, the remote computer loads the instructions into main memory and sends the instructions over a telephone line using a modem. A modem of a local computer system receives the data on the telephone line and uses an infrared transmitter to convert the data to an infrared signal and transmit the infrared signal to a portable computing device, such as a PDA or a laptop. An infrared detector on the portable computing device receives the information and instructions borne by the infrared signal and places the data on a bus. The bus conveys the data to main memory, from which a processor retrieves and executes the instructions. The instructions received by main memory can optionally be stored on storage device either before or after execution by processor.

FIG. 9 illustrates a chip set 900 upon which an embodiment of the invention may be implemented. Chip set 900 is programmed to monitor a sleeping subject as described herein and includes, for instance, the processor and memory components described with respect to FIG. 8 incorporated in one or more physical packages (e.g., chips). By way of example, a physical package includes an arrangement of one or more materials, components, and/or wires on a structural assembly (e.g., a baseboard) to provide one or more characteristics such as physical strength, conservation of size, and/or limitation of electrical interaction. It is contemplated that in certain embodiments the chip set can be implemented in a single chip. Chip set 900, or a portion thereof, constitutes a means for performing one or more steps of FIGS. 3A through 3E.

In one embodiment, the chip set 900 includes a communication mechanism such as a bus 901 for passing information among the components of the chip set 900. A processor 903 has connectivity to the bus 901 to execute instructions and process information stored in, for example, a memory 905. The processor 903 may include one or more processing cores with each core configured to perform independently. A multi-core processor enables multiprocessing within a single physical package. Examples of a multi-core processor include two, four, eight, or greater numbers of processing cores. Alternatively or in addition, the processor 903 may include one or more microprocessors configured in tandem via the bus 901 to enable independent execution of instructions, pipelining, and multithreading. The processor 903 may also be accompanied with one or more specialized components to perform certain processing functions and tasks such as one or more digital signal processors (DSP) 907, or one or more application-specific integrated circuits (ASIC) 909. A DSP 907 typically is configured to process real-world signals (e.g., sound) in real time independently of the processor 903. Similarly, an ASIC 909 can be configured to performed specialized functions not easily performed by a general purposed processor. Other specialized components to aid in performing the inventive functions described herein include one or more field programmable gate arrays (FPGA) (not shown), one or more controllers (not shown), or one or more other special-purpose computer chips.

The processor 903 and accompanying components have connectivity to the memory 905 via the bus 901. The memory 905 includes both dynamic memory (e.g., RAM, magnetic disk, writable optical disk, etc.) and static memory (e.g., ROM, CD-ROM, etc.) for storing executable instructions that when executed perform the inventive steps described herein for biometric monitoring. The memory 905 also stores the data associated with or generated by the execution of the inventive steps.

While certain exemplary embodiments and implementations have been described herein, other embodiments and modifications will be apparent from this description. Accordingly, the invention is not limited to such embodiments, but rather to the broader scope of the presented claims and various obvious modifications and equivalent arrangements.

To the extent the aforementioned embodiments collect, store or employ personal information provided by individuals, it should be understood that such information shall be used in accordance with all applicable laws concerning protection of personal information. Additionally, the collection, storage and use of such information may be subject to consent of the individual to such activity, for example, through well known "opt-in" or "opt-out" processes as may be appropriate for the situation and type of information. Storage and use of personal information may be in an appropriately secure manner reflective of the type of information, for example, through various encryption and anonymization techniques for particularly sensitive information.

What is claimed is:

1. A method comprising:
   receiving, by a device, an input indicating an attachment position of a monitoring device on a body of a subject;
   calibrating, by the device, a resting position of the subject based on the attachment position;
   receiving, by the device and based on calibrating the resting position, sensor information from the monitoring device,
   the sensor information including at least one of accelerometer data or biometric data;
   determining, by the device and based on receiving the sensor information, a movement of the subject from the resting position to a different position; and
   causing, by the device and based on determining the movement of the subject from the resting position to the different position, an image of the subject to be provided on a display.

2. The method of claim 1, where the sensor information includes biometric data, and
   where causing the image of the subject to be provided on the display comprises:
   causing the image of the subject to be provided on a display of a user interface,
   the user interface displaying the image of the subject, and the biometric data, and
   the input indicating the attachment position of the monitoring device being received via the user interface.

3. The method of claim 1, where the sensor information includes accelerometer data and biometric data.

4. The method of claim 3, further comprising:
   determining that the different position is a potentially dangerous position based on the accelerometer data and the biometric data.

5. The method of claim 4, further comprising:
   determining a downward trend of the biometric data; and
   where determining that the different position is the potentially dangerous position comprises:
   determining that the different position is the potentially dangerous position based on the downward trend.

6. The method of claim 4, further comprising:
   analyzing the image of the subject to confirm that the different position is the potentially dangerous position.

7. The method of claim 1, where the sensor information further includes at least one of:
   blood pressure data,
   pulse data,
   temperature data,
   sleeping position data,
   oxygen level data,
   breathing pattern data,
   sleeping pattern data, or
   heart pattern data.

8. A device comprising:
   a memory to store instructions; and
   at least one processor to execute the instructions to:

receive an input indicating an attachment position of a monitoring device on a body of a subject;

calibrate a resting position of the subject based on the attachment position;

receive, based on calibrating the resting position, sensor information from the monitoring device,
the sensor information including at least one of accelerometer data or biometric data;

determine, based on receiving the sensor information, a movement of the subject from the resting position to a different position; and cause, based on determining the movement of the subject from the resting position to the different position, an image of the subject to be provided on a display.

9. The device of claim 8, where the sensor information includes biometric data, and
where the at least one processor, when causing the image of the subject to be provided on the display, is to:
cause the image of the subject to be provided on a display of a user interface,
the user interface displaying the image of the subject and the biometric data, and
the input indicating the attachment position of the monitoring device being received via the user interface.

10. The device of claim 8, where the sensor information includes accelerometer and biometric data.

11. The device of claim 10, where the at least one processor is further to:
determine that the different position is a potentially dangerous position based on the accelerometer data and the biometric data.

12. The device of claim 11, where the at least one processor is further to:
determine a downward trend of the biometric data; and
where the at least one processor, when determining that the different position is the potentially dangerous position, is to:
determine that the different position is the potentially dangerous position based on the downward trend.

13. The device of claim 11, where the at least one processor is further to:
analyze the image of the subject to confirm that the different position is the potentially dangerous position.

14. The device of claim 8, where the sensor information further includes at least one of:
blood pressure data,
pulse data,
temperature data,
sleeping position data,
oxygen level data,
breathing pattern data,
sleeping pattern data, or
heart pattern data.

15. A computer-readable medium storing instructions, the instructions comprising:
one or more instructions that, when executed by a processor, cause the processor to:
receive an input indicating an attachment position of a monitoring device on a body of a subject,
calibrate a resting position of the subject based on the attachment position,
receive, based on calibrating the resting position, sensor information from the monitoring device,
the sensor information including at least one of accelerometer data or biometric data;
determine, based on receiving the sensor information, a movement of the subject from the resting position to a different position; and
cause, based on determining the movement of the subject from the resting position to the different position, an image of the subject to be provided on a display.

16. The computer-readable medium of claim 15, where the sensor information includes biometric data, and
where the one or more instructions, that cause the processor to cause the image of the subject to be provided on the display, cause the processor to:
cause the image of the subject to be provided on a display of a user interface,
the user interface displaying the image of the subject and the biometric data, and
the input indicating the attachment position of the monitoring device being received via the user interface.

17. The computer-readable medium of claim 15, where the sensor information includes accelerometer data and biometric data.

18. The computer-readable medium of claim 17, where the one or more instructions, when executed by the processor, further cause the processor to:
determine that the different position is a potentially dangerous position based on the accelerometer data and the biometric data.

19. The computer-readable medium of claim 18, where the one or more instructions, when executed by the processor, further cause the processor to:
determine a downward trend of the biometric data; and
where the one or more instructions, that cause the processor to determine that the different position is the potentially dangerous position, cause the processor to:
determine that the different position is the potentially dangerous position based on the downward trend.

20. The computer-readable medium of claim 18, where the one or more instructions, when executed by the processor, further cause the processor to:
analyze the image of the subject to confirm that the different position is the potentially dangerous position.

* * * * *